United States Patent [19]

Muraoka

[11] 4,319,876
[45] Mar. 16, 1982

[54] AUXILIARY INSTRUMENT FOR DENTAL TREATMENT

[75] Inventor: Hiroshi Muraoka, Tokyo, Japan

[73] Assignee: Katumi Takahashi, Tokyo, Japan; a part interest

[21] Appl. No.: 167,755

[22] Filed: Jul. 14, 1980

[30] Foreign Application Priority Data

Jul. 23, 1979 [JP] Japan .................................. 54-93525
Oct. 17, 1979 [JP] Japan ................................ 54-142720

[51] Int. Cl.³ ............................................. A61C 31/00
[52] U.S. Cl. ...................................... 433/141; 433/72
[58] Field of Search .................. 433/68, 140, 72, 141; 128/89 A

[56] References Cited

U.S. PATENT DOCUMENTS 757,133  4/1904  Marshall .............................. 433/68
1,044,206 11/1912 Little .................................... 433/68

Primary Examiner—Robert Peshock
Attorney, Agent, or Firm—Watts, Hoffmann, Fisher & Heinke Co.

[57] ABSTRACT

An auxiliary instrument for dental treatment comprises a forked mandible retaining plate abutting on the face under the mandible and a protruding mandible head retaining means provided in the vicinity of the forked base end portion of said mandible retaining plate and having a through opening into which the head of mandible is inserted. A flexible substance is placed on the surface of said mandible retaining plate as well as the inner peripheral surface of said mandible head retaining means and can be removed freely as occasion demands.

2 Claims, 7 Drawing Figures

AUXILIARY INSTRUMENT FOR DENTAL TREATMENT

BACKGROUND OF THE INVENTION

This invention relates to an auxiliary instrument for dental treatment adapted for guiding the centric relation or terminal hinge position of the mandible, of which dentistry requires consideration, into the most suitable position.

Three broad and general classifications for terminal hinge position are currently recognized, that is, the most retruded position of the mandible (Ligmental position), occlusion in light contact (Muscular position) and upper most position of the condyle (Upper most position).

The guidance of terminal hinge position (centric relation) has higherto been effected by the patient himself in the manner of supporting the mandible using forefingers and thumbs as well as holding the head of the mandible using thumbs and moving the position in a suitable direction relative to the maxilla such as before and behind, up and down or the like. However, in case where the patient must determine for himself the centric relation by using his fingers it has hitherto been observed that there often takes place the irregularity of centric relation in accordance with the degree of skill of the patient and accordingly the reproducibility of centric relation is hindered, thereby rendering the dental treatment per se unstable. In other words, an auxiliary instrument for dental treatment has hitherto been not proposed which is suitably adapted for assisting the practitioner in guiding the centric relation of the mandible into the most suitable position.

SUMMARY OF THE INVENTION

It is an object of this invention to provide a novel auxiliary instrument for dental treatment which can facilitate the guidance of the centric relation of the mandible into the most suitable position in the manner of moving the mandible in a suitable direction relative to the maxilla in place of the manner of guiding the centric relation of the mandible with resort to person's fingers exclusively.

Another object of this invention is to provide an auxiliary instrument for dental treatment which comprises composite members to be assembled with ease and thus is adaptable for the different-shaped mandibles.

A further object of this invention is to provide an auxiliary instrument for dental treatment in which a flexible substance is placed, in freely removable manner, on the surface of a mandible retaining plate as well as the inner peripheral surface of a mandible head retaining means so that said instrument can stick fast to the mandible, irrespective of its size, and support it positively.

DETAILED DESCRIPTION OF THE INVENTION

Figure 1:
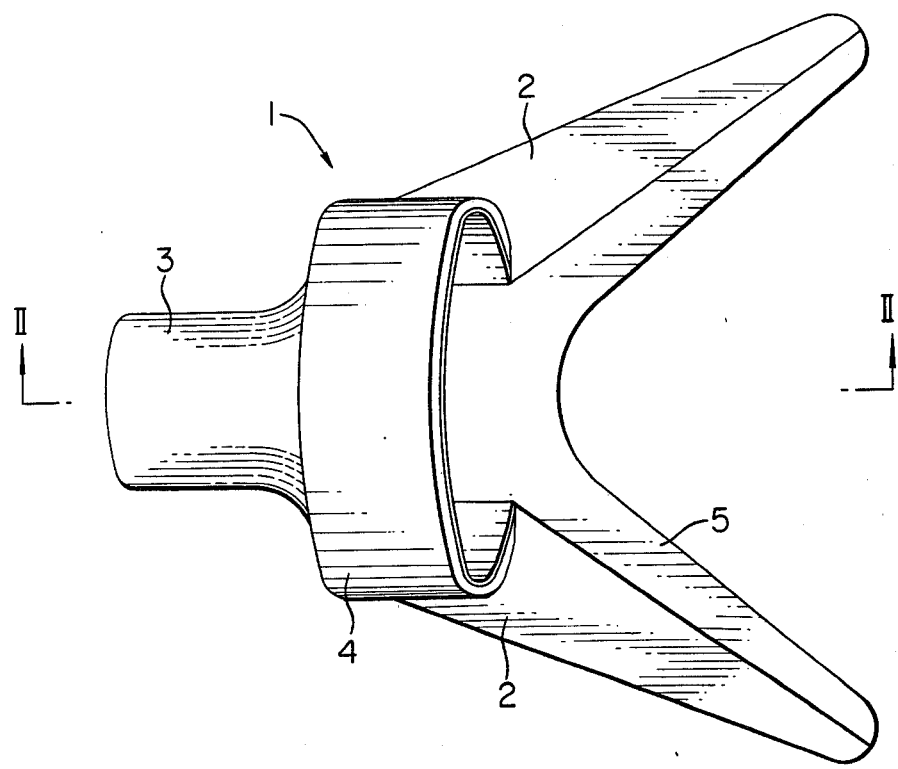
FIG. 1 is a plan view of a first embodiment of the auxiliary instrument for dental treatment according to this invention.
Figure 2:
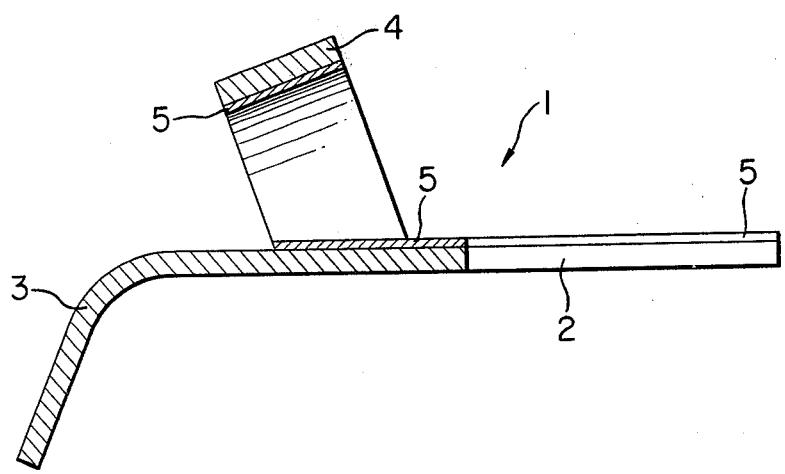
FIG. 2 is a vertical longitudinal sectional view taken on line II—II of FIG. 1.
Figure 3:
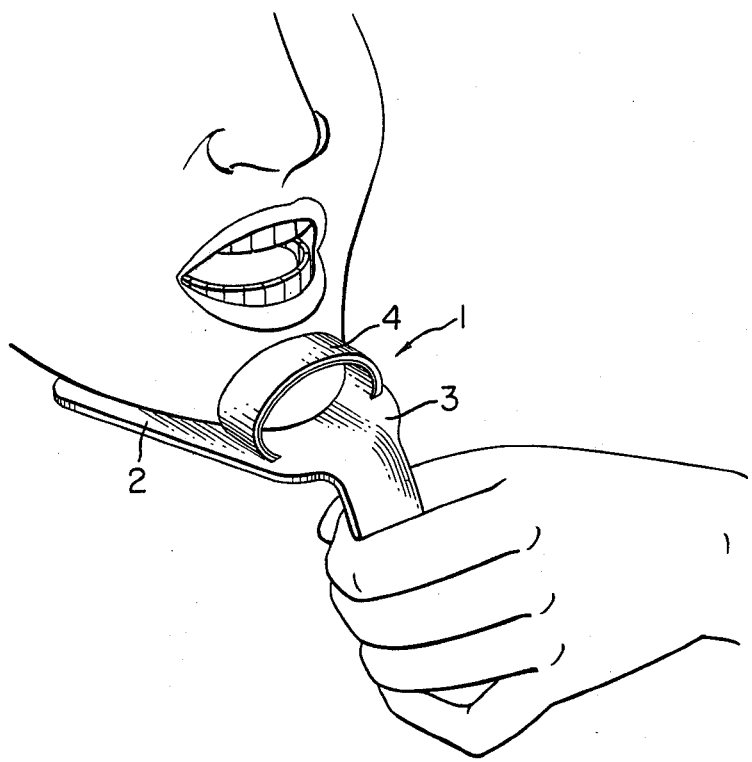
FIG. 3 is a slant view illustrating its state in use.
Figure 4:
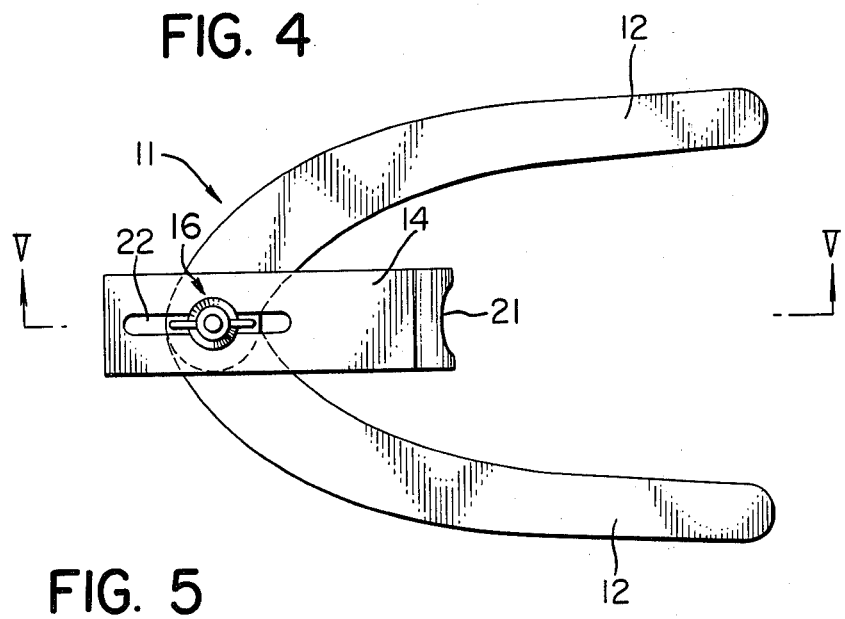
FIG. 4 is a plan view of a second embodiment of the auxiliary instrument for dental treatment according to this invention.
Figure 5:
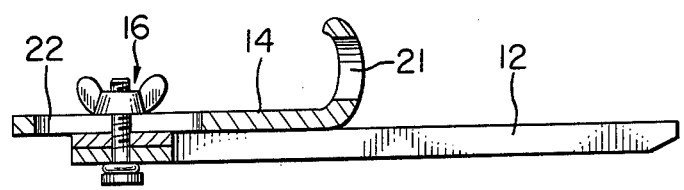
FIG. 5 is a vertical longitudinal sectional view taken on line V—V of FIG. 4.

FIGS. 1 through 3 illustrate the first embodiment of the auxiliary instrument according to this invention.

Reference numeral 1 denotes an auxiliary instrument body having a fixed length and comprising a flat body of synthetic resin or the like. This body 1 defines at the fore part a forked mandible retaining plate 2, 2 abutting on the face under the mandible and also defines at the rear part a handle 3 with its end curved downwardly by slow degrees. And, in the vicinity of the forked base portion of said mandible retaining plate 2, 2 locating substantially in the center of the body 1 there is provided, slightly bending backward, a mandible head retaining means 4 having an arched peripheral wall into which the head of mandible is inserted. In the body 1, furthermore, a flexible substance 5 having a thickness of about 1 mm is placed, in freely removable manner, on the confronting inside surface of the mandible retaining plate 2, 2 and the inside peripheral surface of the mandible head retaining means 4. The flexible substance thus ensures the adaptation of the body to the different shaped mandibles and, unless needed, may be removed for sterilizing purposes. In this context, it goes without saying that the flexible substance 5 may be placed not only on the confronting inside surface of the mandible retaining plate 2, 2 but also, for instance, on the whole surface of the retaining plate 2, 2.

Next, reference will be made as to how to use the above device.

As shown in FIG. 3, the body 1 is first placed under the mandible of the patient by means of the handle 3, and then the mandible retaining plate 2, 2 is advanced while abutting on the face under the mandible such that the mandible head retaining means 4 may cover the head of the mandible. Thus, the mandible as a whole is not only firmly fixed to the body 1 but also is closely held by the action of said flexible substance 5 placed on the mandible retaining plate 2, 2 and the mandible head retaining means 4. Then, the body 1, which has supported the mandible as aforesaid, is moved in a suitable direction relative to the maxilla such as front and rear, up and down or the like, whereby it is rendered possible to guide the centric relation of mandible into a most suitable position.

In FIGS. 4 through 7 there is illustrated the second embodiment of the auxiliary instrument for dental treatment according to this invention. This auxiliary instrument for dental treatment is differentiated from that of the first embodiment in that the composite elements of the former are intended to be assembled.

Figure 6:
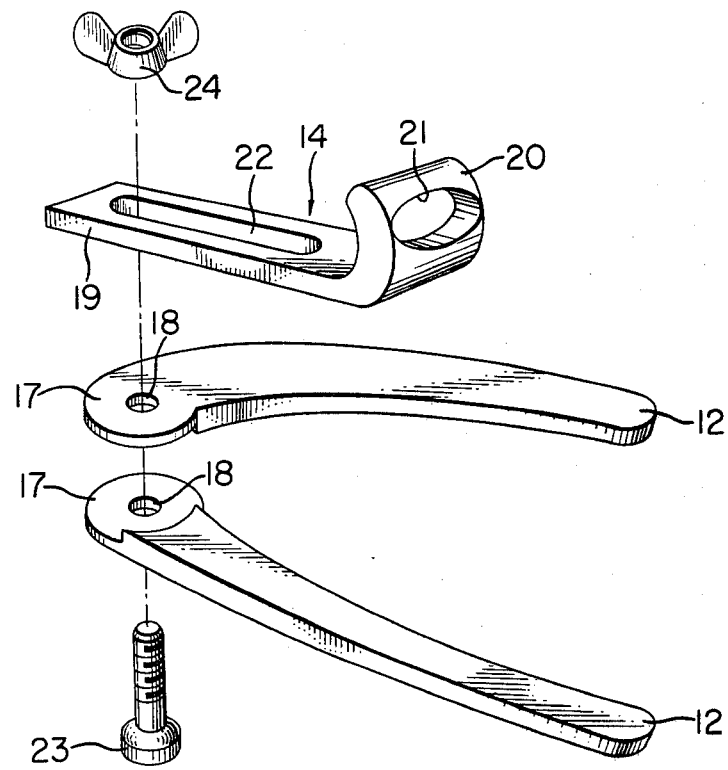
FIG. 6 is a slant view illustrating composite members in disassembled state.

As is clearly seen from FIG. 6, this auxiliary instrument body 11 for dental treatment comprises a forked mandible retaining plate set 12, 12 abutting on the face under the mandible, a protruding mandible head retaining means 14 provided in the vicinity of the forked base end portion 17 of said mandible retaining plate set 12, 12 and a clamping means 16 for clamping said mandible retaining plate set 12, 12 and mandible head retaining means 14. The base end portion 17 of each mandible retaining plate 12 is made round and its confronting, overlapping face is made to have a cutaway thickness of about ½ of that of the mandible retaining plate 12. Further, said base end portion 17 has in its center an opening through which the clamping means is inserted, and the mandible retaining plate is arranged so that it may be opened or shut by the aid of the clamping means 16. The mandible head retaining means 14 comprises a horizontal base plate 19 and a protruding, substantially L-shaped plate 20 which is defined at the end portion of said base plate in the manner of curving upward by slow degrees, said protruding plate 20 having an ellipstical through opening 21 through which the head of the mandible is inserted. Still further, a slit 22 is perforated lengthwise in the horizontal base plate 19, the width of said slit being sufficient for slidable movement of the clamping means 16, whereby said mandible head retaining means 14 is allowed to go ahead and back from the base end portion 17 of the mandible retaining plate set 12, 12 against the fore end direction thereof.

In this context, it is to be noted that the same flexible substance being about 1 mm in thickness as used in Example 1 may be placed, in freely removable manner, on the confronting inside surface of the mandible retaining plate set 12, 12 of the body 11 as well as the inside peripheral surface of the through hole 21 in the mandible head retaining means 14, and said flexible substance should not be restricted to the aforegoing, that is, may, as mentioned in Example 1, be placed on the whole surface of the mandible retaining plate set 12, 12.

Hereinafter, reference will be made as to how to use the above device.

Figure 7:
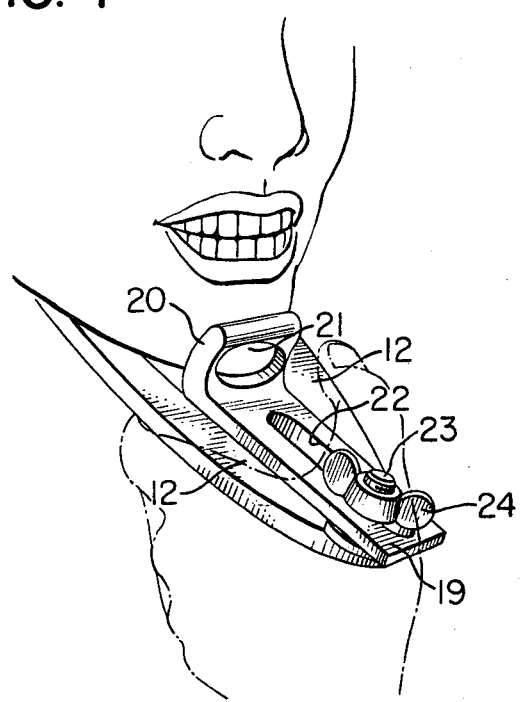
FIG. 7 is a slant view illustrating its state in use.

First, each base end portion 17 of the mandible retaining plate set 12, 12 is overlapped, a bolt 23 is inserted into the opening 18 defined in the center of said each base end portion 17, this bolt 23 is allowed to insert through the slit 22 of the horizontal base plate 19, and then a butterfly nut 24 is screwed into the bolt 23. Assembling of the body 11 is thus completed. And, controlling of the butterfly nut 24 makes it possible to open and shut the mandible retaining plate set 12, 12 in an optional degree for well fitting the different-shaped mandibles and further to locate the mandible end retaining means 14 at an optional ahead or back position. Referring to how to use after such arrangement, as illustrated in FIG. 7, first the rear part of the mandible retaining plate set 12, 12 is grasped by hand and then held so that the fore part of the mandible retaining plate set 12, 12 may abut on the mandible as well as the head of the mandible may be inserted into the through opening 21 of the mandible head retaining means 14. Thus, the mandible as a whole is firmly fixed to the body 11. Then, the body 11, which has supported the mandible as aforesaid, is moved in a suitable direction relative to the maxilla such as front and rear, up and down or the like, whereby it is rendered possible to guide the centric relation of mandible into a most suitable position.

What is claimed is:

1. An auxiliary instrument for dental treatment which comprises a forked mandible retaining plate with a surface for abutting the face under the mandible and extending under the mandible on opposite sides, a protruding mandible head retaining means extending from the plate in the vicinity of a forked base end portion thereof, said means having a through opening into which the head of the mandible is inserted, a flexible substance removably carried on the surface of said mandible retaining plate and on an inside peripheral surface of said mandible head retaining means that forms said through opening and means for gnipping said instrument to guide said mandible.

2. An auxiliary instrument for dental treatment as claimed in claim 1 in which said mandible retaining plate comprises a set of plate members arranged to be opended and shut by the aid of a clamping means disposed at the base end portion thereof and said mandible head retaining means is arranged to go ahead and back from the end portion of the mandible retaining plate against the fore end direction thereof by the aid of the clamping means.

* * * * *